United States Patent
Nguyen et al.

(10) Patent No.: US 6,878,839 B2
(45) Date of Patent: Apr. 12, 2005

(54) METHOD FOR PREPARING ORGANOFUNCTIONAL SILANES

(75) Inventors: Binh Thanh Nguyen, Midland, MI (US); John Patrick Cannady, Midland, MI (US)

(73) Assignee: Dow Corning Corporation, Midland, MI (US)

(*) Notice: Subject to any disclaimer, the term of this patent is extended or adjusted under 35 U.S.C. 154(b) by 114 days.

(21) Appl. No.: 10/269,241

(22) Filed: Oct. 11, 2002

(65) Prior Publication Data

US 2004/0073053 A1 Apr. 15, 2004

(51) Int. Cl.$^7$ .................................................. C07F 7/18
(52) U.S. Cl. ...................................................... 556/471
(58) Field of Search .......................................... 556/471

(56) References Cited

U.S. PATENT DOCUMENTS

| | | | |
|---|---|---|---|
| 2,927,938 A | 3/1960 | Cohen et al. | 260/448.8 |
| 3,403,050 A | 9/1968 | Chadha | 117/161 |
| 4,173,576 A | * 11/1979 | Seiler et al. | 556/471 |
| 4,268,682 A | 5/1981 | Oswald et al. | 556/465 |
| 4,506,087 A | * 3/1985 | Fischer et al. | 556/471 |
| 5,338,876 A | 8/1994 | Jung et al. | 556/431 |

\* cited by examiner

*Primary Examiner*—Peter O'Sullivan
(74) *Attorney, Agent, or Firm*—Jim L. DeCesare

(57) ABSTRACT

Alkenylalkoxysilanes such as allyltrimethoxysilane can be made by reacting the corresponding monoalkenyldichlorosilane, i.e., allyldichlorosilane, with a monohydroxy alcohols, i.e., methyl alcohol. No catalyst is required and the reactions can be carried out at room temperature.

4 Claims, No Drawings

METHOD FOR PREPARING ORGANOFUNCTIONAL SILANES

FIELD OF THE INVENTION

This invention is related to methods for preparing certain organofunctional silanes by an alkoxylation process, more particularly by methoxylation.

BACKGROUND OF THE INVENTION

Organofunctional silanes are useful in a variety of applications including their use as reducing agents, silylating agents, water repellents, coupling agents, crosslinking agents, and as monomers for preparing polysiloxanes of varying consistency. Therefore, there is always an existing need for more efficient methods for their preparation, and for more simplified and less expensive processes for preparing these silanes.

While the state of the art includes known processes for preparing silanes by the alkoxylation of trichlorosilanes, for example, U.S. Pat. No. 2,927,938 (Mar. 8, 1960), no process is in the public domain relative to preparing organofunctional silanes containing unsaturated groups, by alkoxylation of unsaturated dichlorosilanes. Typically, such alkenyl functional alkoxysilanes are prepared by Grignard reactions involving the reaction of allyl chloride with magnesium, and tetraalkoxysilanes such as tetramethoxysilane and tetraethoxysilane, as described for example in U.S. Pat. No. 3,403,050 (Sep. 24, 1968).

SUMMARY OF THE INVENTION

The invention is directed to a method of making organofunctional silanes by reacting monoalkenyldichlorosilanes with monohydroxy alcohols to form alkenylalkoxysilanes.

Monoalkenyldichlorosilanes such as allyldichlorosilane and monohydroxy alcohols such as methyl alcohol are among the reaction components most preferred. In this regard, allyltrimethoxysilane would be obtained.

These and other features of the invention will become apparent from a consideration of the detailed description.

DETAILED DESCRIPTION OF THE INVENTION

The process according to this invention involves the preparation of organofunctional silanes such as alkenylalkoxysilanes by reacting monoalkenyldichlorosilanes with monohydroxy alcohols. The process is illustrated below in the equation:

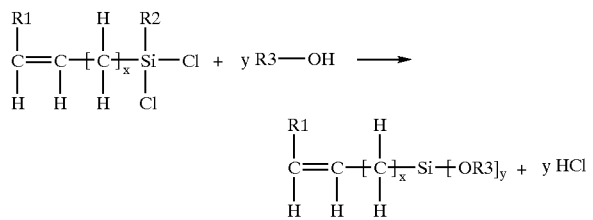

In the above equation, R1 represents hydrogen or an alkyl group having 1-6 carbon atoms such as methyl, ethyl, propyl, isopropyl, butyl, isobutyl, pentyl, and hexyl, or R1 can be a cycloalkyl group such as cyclobutyl, cyclopentyl, and cyclohexyl; R2 represents hydrogen; R3 represents an alkyl group containing 1–6 carbon atoms such as methyl, ethyl, propyl, isopropyl, butyl, isobutyl, pentyl, and hexyl, a cycloalkyl group such as cyclobutyl, cyclopentyl, and cyclohexyl, or an allyl group; x is 0–4; and y is 3.

Some representative examples of suitable monoalkenyidichlorosilanes include vinyldichlorosilane $CH_2=CHSiHCl_2$, allyldichlorosilane $CH_2=CHCH_2SiHCl_2$, 2-butenyidichlorosilane $CH_3CH=CHCH_2SiHCl_2$, 3-butenyidichlorosilane $CH_2=CHCH_2CH_2SiHCl_2$, and 5-hexenyidichlorosilane $CH_2=CH(CH_2)_4SiHCl_2$.

Some representative monohydroxy alcohols which can be employed include methyl alcohol, ethyl alcohol, propyl alcohol, isopropyl alcohol, cyclobutanol, cyclopentanol, cyclohexanol, and allyl alcohol.

Components such as these can render alkenylalkoxysilanes such as vinyltrimethoxysilane, vinyltriethoxysilane, vinyltripropoxysilane, vinyltributoxysilane, vinyltripentoxysilane, vinyltrihexoxysilane, allyltrimethoxysilane, allyltriethoxysilane, allyltripropoxysilane, allyltributoxysilane, allyltripentoxysilane, allyltrihexoxysilane, 2-butenyltrimethoxysilane, 2-butenyltriethoxysilane, 2-butenyltripropoxysilane, 2-butenyltributoxysilane, 2-butenyltripentoxysilane, 2-butenyltrihexoxysilane, 5-hexenyltrimethoxysilane, 5-hexenyltriethoxysilane, 5-hexenyltripropoxysilane, 5-hexenyltributoxysilane, 5-hexenyltripentoxysilane, and 5-hexcnyltrihexoxysilane.

Some additional alkenylalkoxysilanes which can be prepared, depending on which alcohol is used, include allyltricyclobutoxysilane, allyltricyclopentoxysilane, allylcyclohexcnyloxysilane, allyltrialloxysilane, 3-butenyltributoxysilane, 3-butenyltripentoxysilane, 3-butenyltrihexoxysilane, 3-butenyltributoxysilane, 3-butenyltripentoxysilane, 3-butenyltrihexoxysilane, 3-butenyltrialloxysilane, 2-butenyltributoxysilane, 2-butenyltripentoxysilane, 2-butenyltrihexoxysilane, 2-butenyltrialloxysilane, 5-hexenyltricyclobutoxysilane, 5-hexenyltricyclopentoxysilane, 5-hexenyltricyclohexenyloxysilane, and 5-hexenylitrialloxysilane.

Thus, in a particular one of the preferred embodiments of the invention, allyldichlorsilane is reacted with methyl alcohol to produce allyltrimethoxysilane and hydrogen, as shown in the equation below:

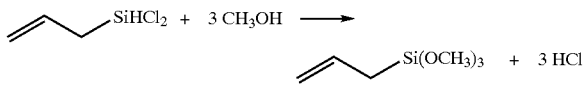

The starting monomer allydichlorosilane is commercially available, or it can be prepared by reacting elemental silicon simultaneously with allyl chloride and hydrochloric acid, as described, for example, in U.S. Pat. No. 5,338,876 (Aug. 16, 1994), and according to the equation:

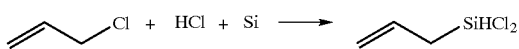

The relative amount of the monoalkenyidichlorosilane and the monohydroxy alcohol used according to the invention can be varied. While there is no requirement that the reaction be carried out under stoichiometric conditions, it is preferred that the reaction be conducted using a stoichiometric excess of the monohydroxy alcohol. Most preferred, therefore, is to carry out the reaction using about a 0.1–10 percent stoichiometric excess of the monohydroxy alcohol. The reaction requires no catalyst, and while the process can be carried out batch-wise, semi-continuously, or continuously, batch processing is most preferred.

Contact between the monoalkenyldichlorosilane and the monohydroxy alcohol can occur at a temperature between −80 to 350° C., preferably between 20–250° C., but most preferably at about room temperature, i.e., 20–25° C./68–77° F.

The optimum reaction time is variable depending upon the reactants, the reaction temperature, and the concentration of the monoalkenyldichlorosilane and the monohydroxy alcohol. Ordinarily, there is no benefit in extending the contact time of the reactants beyond about 24 hours, but likewise there is usually no harm, unless extremely low temperatures are employed. With most of the particular reactants used herein, practical quantitative yields can be obtained in about 4 hours.

The reaction can be carried out at atmospheric, sub-atmospheric, or super-atmospheric pressure. Here again, the choice of conditions is largely a matter of logic, based upon the nature of the reactants, and the equipment available. Non-volatile reactants are especially adaptable to being heated at atmospheric pressure with or without a reflux arrangement. Reactants which are gaseous at ordinary temperatures are preferably reacted at substantially constant volume under autogenous or induced pressure. The best results are obtained by maintaining all reactants in the liquid phase.

EXAMPLES

The following example is set forth in order to illustrate the invention in more detail.

Example 1

Preparation of Allyltrimethoxysilane

The apparatus used in this example consisted of a three-neck 100 mL round-bottom flask resting on a heating mantle, a jack having a magnetic stirring bar, an addition funnel, a reflux condenser, a thermometer, and a nitrogen inlet system.

Into the flask was loaded 12.6 gram/0.9 mole of allyldichlorosilane. Into the addition funnel was loaded 8.57 gram/0.26 mole of methyl alcohol. The methyl alcohol was then added to the allyldichlorosilane in the flask drop wise at room temperature. The addition of methyl alcohol to the flask took about 20 minutes to complete. It was observed that the reaction was slightly exothermic. Hydrogen chloride was generated and removed from the flask by sparging with nitrogen. Analysis of the reaction mixture by Gas Chromatography (GC) showed that it contained about a 40 percent GC area percent of allyltrimethoxysilane, with the remainder being unreacted methyl alcohol and 3-methoxypropyltrimethoxysilane $CH_3O(CH_2)_3Si(OCH_3)_3$. The presence of allyltrimethoxysilane in the reaction mixture was confirmed by Gas Chromatography/Mass Spectrometry (GC/MS) analysis.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A method of making an organofunctional silane comprising
    reacting a monoalkenyldichlorosilane with a monohydroxy alcohol having 1–6 carbon atoms to form a alkenylalkoxysilane, and separating the alkenylalkoxysilane from the reaction mixture, the monoalkenyldichlorosilane being selected from the group consisting of allyldichlorosilane, 2butenyldichlorosilane, 3-butenyldichlorosilane, and 5-hexenyldichlorosilane.

2. A method according to claim 1 in which the monohydroxy alcohol is selected from the group consisting methyl alcohol, ethyl alcohol, propyl alcohol, isopropyl alcohol, allyl alcohol, cyclobutanol, cyclopentanol, and cyclohexanol.

3. A method according to claim 1 in which the alkenylalkoxysilane is selected from the group consisting of allyltrimethoxysilane, allyltrimethoxysilane, allyltriethoxysilane, allyltriprpoxysilane, allyltributoxysilane, allyltripeontoxysilane, allyltrihexoxysilane, 2-butenyltrimethoxysilane, 2-butenyltriethoxysilm, 2-butenyltripropoxysilane, 2-butenyltributoxysilane, 2-butenyltripentoxysilane, 2-butenyltrihexoxysilane, 5-hexenyltrimethoxysilane, 5-hexenyltriethoxysilane, 5-hexenyltripropoxysilane, 5-hexenyltributoxysilane, 5-hexenyltripentoxysilane, 5-hexenyltrihexoxysilane, allyltricyclobutoxysilane, allyltricyclopentoxysilane, allylcyclohexcnyloxysilane, allyltrialloxysilane, 3-butenyltributoxysilane, 3-butenyltripentoxysilane, 3-butenyltrihexoxysilane, 3-butenyltributoxysilane, 3-butenyltripentoxysilane, 3-butenyltrihexoxysilane, 3-butenyltrialloxysilane, 2-butenyltributoxysilane, 2-butenyltripentoxysilane, 2butenyltrihexoxysilane, 2-butenyltrialloxysilane, 5-hexenyltricyclobutoxysilane, 5-hexenyltricyclopentoxysilane, 5-hexenyltricyclohexenyloxysilane, and 5-hexenylitrialloxysilane.

4. A method of making allyltrimethoxysilane comprising reacting allyldichlorosilane with methyl alcohol without a catalyst at room temperature and separating allyltrimethoxysilane from the reaction mixture.

* * * * *